United States Patent
Lawson et al.

(10) Patent No.: US 7,052,906 B1
(45) Date of Patent: May 30, 2006

(54) SYNTHETIC TRANSMEMBRANE COMPONENTS

(75) Inventors: Alastair David Griffiths Lawson, Alresford (GB); Helene Margaret Finney, Maidenhead (GB)

(73) Assignee: Celltech R & D Limited, Slough (GB)

( * ) Notice: Subject to any disclaimer, the term of this patent is extended or adjusted under 35 U.S.C. 154(b) by 0 days.

(21) Appl. No.: 09/958,646

(22) PCT Filed: Apr. 17, 2000

(86) PCT No.: PCT/GB00/01476

§ 371 (c)(1),
(2), (4) Date: Oct. 11, 2001

(87) PCT Pub. No.: WO00/63374

PCT Pub. Date: Oct. 26, 2000

(30) Foreign Application Priority Data

Apr. 16, 1999 (GB) .................................. 9908816.3
Apr. 16, 1999 (GB) .................................. 9908818.9

(51) Int. Cl.
C12N 15/85 (2006.01)
C12N 15/63 (2006.01)
C07H 21/04 (2006.01)
C07K 14/00 (2006.01)
A61K 38/00 (2006.01)

(52) U.S. Cl. .............. 435/325; 435/252.3; 435/254.11; 435/254.2; 435/320.1; 536/23.4; 530/350; 514/2; 514/13

(58) Field of Classification Search ................ 536/234, 536/235, 23.1; 435/320.1, 325; 530/350; 514/2, 44
See application file for complete search history.

(56) References Cited

FOREIGN PATENT DOCUMENTS

| WO | WO 96/23881 | | 8/1996 |
|---|---|---|---|
| WO | WO 96 23881 A | * | 8/1996 |
| WO | WO 97/23613 | | 7/1997 |
| WO | WO 97 23613 A | * | 7/1997 |
| WO | WO 99/57268 | | 11/1999 |
| WO | WO 00/63372 | | 10/2000 |

OTHER PUBLICATIONS

Marra et al. EMBL database, Accession No: AA444968, Jun. 3, 1997.*
Fire et al. A modular set of lac Z fusion vectors for studying gene expression i *Caenorhabditis elegans*. Gene 93:189-198, 1990.*
Killian et al. Induction of nonbilayer structures in diacylphosphatidylcholine model membranes by transmembrane alpha-helical peptides: importance of hydrophobic mismatch and proposed role of Tryptophans. Biochemistry 35: 1037-1045, 1996.*
Eshhar, Z. Cancer Immunol. Immunother. 45:131-136, 1997.*
Sean Munro Sequences within and adjacent to the transmembrane segment of alpha-2,6-sialyltransferase specify Golgi retention. EMBO 10:3577-3588, 1991.*
Finney et al. Chimeric receptors providing both primary and costimulatory signaling in T cells from a single gene product. J. Immunol. 161:2791-2797, 1998.*
A. Aruffo, et al., "Molecular cloning of a CD28 cDNA by a high-efficiency COS cell expression system", *PNAS, USA* 1987, 84, 8573-8577.
Bebbington, C.R. "Xpression of antibody genes in nonlymphoid mammalian cells" *Methods: A companion to methods in Enzymology*,1991, 2,136-145.
Eshhar, Z., "Tumor-specific T-bodies: towards clinical application", *Cancer Immunol. Immunother* , 1997, 45, 131-136.
Fire, A. et al., "A modular set of lacZ fusion vectors for studying gene expression in *Caenorhabditis elagans*", *Gene*, 1990, 93, 189-198.
Honsho, M. et al., "Retention of cytochrome b5 in the endoplasmic reticulum is transmembrane and luminal domain-dependent", *The Journal of Bilogical Chemistry*, 1998, 273(33), 20860-20866.
Kuster, H. et al., "Characterization and expression of the gene for the human Fc receptor . . . subunit", *J. Biol. Chem*, 1990, 265, 6448-6452.
Moingeon, P. et al., "Human natural killercells andmature T lymphocytes express identical CD3 subunits as defined by cDNA cloning and sequence analysis", *Eur J. Immunol*, 1990, 20, 1741-1745.
Munro, S., "Sequences within and adjacent to the transmembrane segment of α-2, 6-sialyltransferase specify Golgi retention", *The EMBO Journal*, 1991, 10(12), 3577-3588.
Reithmeier, R., "Characterization and modeling of membrane proteins using sequence analysis", *Current Biology*, 1995, 5, 491-500.
Weissman, A.M..et al., "Molecular cloning and chromosomal localizationof the human T-cell receptor chain: Distinction from the molecular CD3 complex", *PNAS*, 1988, 85, 9709-9713.
Wimley, W.C. et al., "Experimentally determined hydrophobicity scale for proteins at membrane interfaces", *Nature Structural Biology*, 1996, 3, 848-8.

* cited by examiner

*Primary Examiner*—Ruixiang Li
(74) *Attorney, Agent, or Firm*—Woodcock Washburn LLP

(57) ABSTRACT

The invention relates to nucleic acids encoding a synthetic transmembrane region as well as to membrane associated proteins containing these synthetic transmembrane regions. The design of the synthetic transmembrane region allows various properties of a protein, such as its level of expression, and relative response to ligand binding to be tailored as required for a specific purpose.

10 Claims, 7 Drawing Sheets

CLONING CASSETTE FOR CHIMERIC RECEPTOR CONSTRUCTION

FIG. 2

Range: 1 to 200

```
              >SpeI
                  *         10         20              30              40              50              60
                  *          *          *               *               *               *               *
              CG ACT AGT GAC AAA ACT CAC ACA TGC CCA CCG TGC CCA AAA CAC CTT TGT CCA AGT CCC
              GC TGA TCA CTG TTT TGA GTG TGT ACG GGT GGC ACG GGT TTT GTG GAA ACA GGT TCA GGG
                 T   S   D   K   T   H   T   C   P   P   C   P   K   H   L   C   P   S   P>
                                                                                          A6083

>NarI
                     70         80       90  *         100            110             120             130
                      *          *        *  *          *               *               *               *
              CTA TTT CCC GGA CCT TCT AAG CCC GCC TTT GTG CTG GTG GTT GGT GGA GTC CTG GCT
              GAT AAA GGG CCT GGA AGA TTC GGG CGG AAA CAC GAC CAC CAA CCA CCT CAG GAC CGA
                 L   F   P   G   P   S   K   P   A   F   V   L   V   V   G   G   V   L   A>
              S0146                            A6081

>MluI        >BamHI
                    140        150        160            170             180             190
                      *          *          *               *               *               *
              TGC TAT AGC TTG CTA GTA ACA GTG GCC TTT ATT ATT TTC TGG GTG ACG CGT GGA TCC TGA
              ACG ATA TCG AAC GAT CAT CGT CAC CGG AAA TAA TAA AAG ACC CAC TGC GCA CCT AGG ACT
                 C   Y   S   L   L   V   T   V   A   F   I   I   F   W   V   T   R   G   S   *>
                                            A6082

>EcoRI
                  *        200
                  *          *
              GAATTCATA
              CTTAAGTAT
```

FIG. 3

OLIGONUCLEOTIDE SEQUENCES FOR CHIMERIC RECEPTOR CONSTRUCTION

All oligos are listed in the 5' to 3' orientation

S0146:CGACTAGTGACAAAACTCACACATGCCCACCGTGCCCAAAAGGGAAACA
CCTTTGTCCAACTCCC

A6081:GCCTTTTGGGTGCTGGTGGTGGTTGGTGGAGTCCTGGCTTGCTATAGCT
TGCTAGTAACAGTG

A6082:TATGAATTCTCAGGATCCACGCGTCACCCAGAAAATAATAAAGGCCACTG
TTACTAGCAAGCTATAG

A6083:CACCACCAGCACCCAAAAGGCGCCGGGCTTAGAAGGTCCGGGAAATAG
GGGACTTGGAC

A9515:GGCTGATCACGACTGAAGATCCAAGTGCG

A9516:TATGAATTCTCAGGATCCCTGTGGTGGTTTCTCATG

B6463:CGCCTTTTGGGTGCTGCTGCTCCTGCTGCTCCTGCTCCTGCTGCTCCTG
CTGCTGCTCCTGCTACTGCTCCTGCTGCTCCTGCTGCTCTTCTGGGTGA

B6464:CGCGTCACCCAGAAGAGCAGCAGGAGCAGCAGGAGCAGTAGCAGGAGC
AGCAGCAGGAGCAGCAGGAGCAGGAGCAGCAGGAGCAGCAGCACCCAAAAGG

B6465:CGCCTTTTGGGTGCTGCTGCTCCTGCTGCTCCTGCTCCTGCTGCTCCTG
CTGCTGCTCCTGCTACTGCTCCTGCTGCTCCTGTTCTGGGTGA

B6466:CGCGTCACCCAGAACAGGAGCAGCAGGAGCAGTAGCAGGAGCAGCAGC
AGGAGCAGCAGGAGCAGGAGCAGCAGGAGCAGCAGCACCCAAAAGG

B6467:CGCCTTTTGGGTGCTGCTGCTCCTGCTGCTCCTGCTCCTGCTGCTCCTG
CTGCTGCTCCTGCTACTGCTCCTGCTGTTCTGGGTGA

B6468:CGCGTCACCCAGAACAGCAGGAGCAGTAGCAGGAGCAGCAGCAGGAGC
AGCAGGAGCAGGAGCAGCAGGAGCAGCAGCACCCAAAAGG

B6469:CGCCTTTTGGGTGCTGCTGCTCCTGCTGCTCCTGCTCCTGCTGCTCCTG
CTGCTGCTCCTGCTACTGTTCTGGGTGA

B6470:CGCGTCACCCAGAACAGTAGCAGGAGCAGCAGCAGGAGCAGCAGGAGC
AGGAGCAGCAGGAGCAGCAGCACCCAAAAGG

B6471:CGCCTTTTGGGTGCTGCTGCTCCTGCTGCTCCTGCTCCTGCTGCTCCTG
CTGCTGTTCTGGGTGA

B6472:CGCGTCACCCAGAACAGCAGCAGGAGCAGCAGGAGCAGGAGCAGCAGG
AGCAGCAGCACCCAAAAGG

C3208:TATGAATTCTCAGGATCCGCGAGGGGGCAGGGCCTG

C3209:GTGACGCGTGGATCAAGAGTGAAGTTCAGCAGGAGC

FIG. 4
SYNTHETIC TRANSMEMBRANE COMPONENTS

FWVLLLLLLLLLLLLLFWV  TM20

FWVLLLLLLLLLLLLLLLLLFWV  TM24

FWVLLLLLLLLLLLLLLLLLLLLFWV  TM27

FWVLLLLLLLLLLLLLLLLLLLLLLFWV  TM29

FWVLLLLLLLLLLLLLLLLLLLLLLLLFWV  TM31

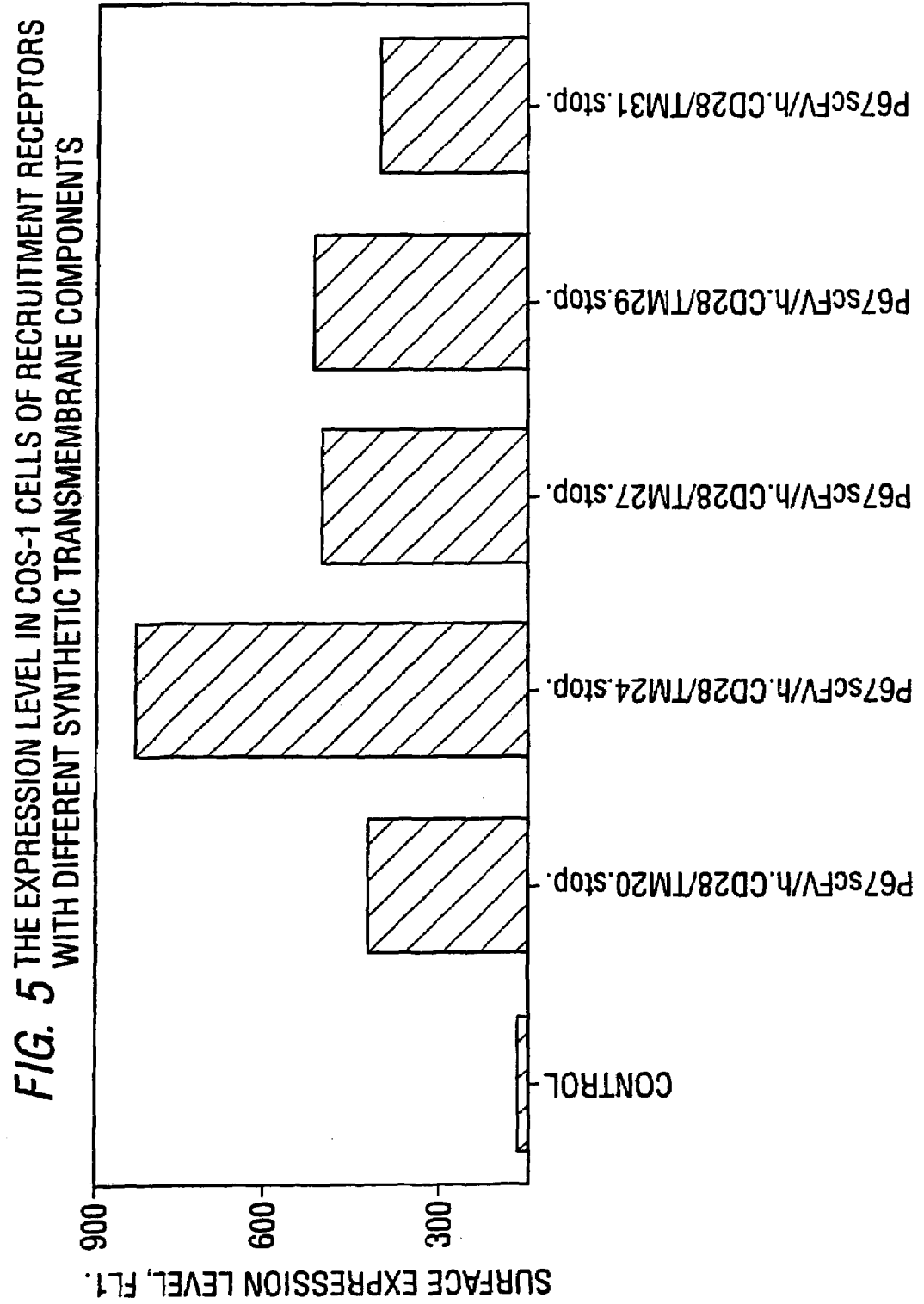

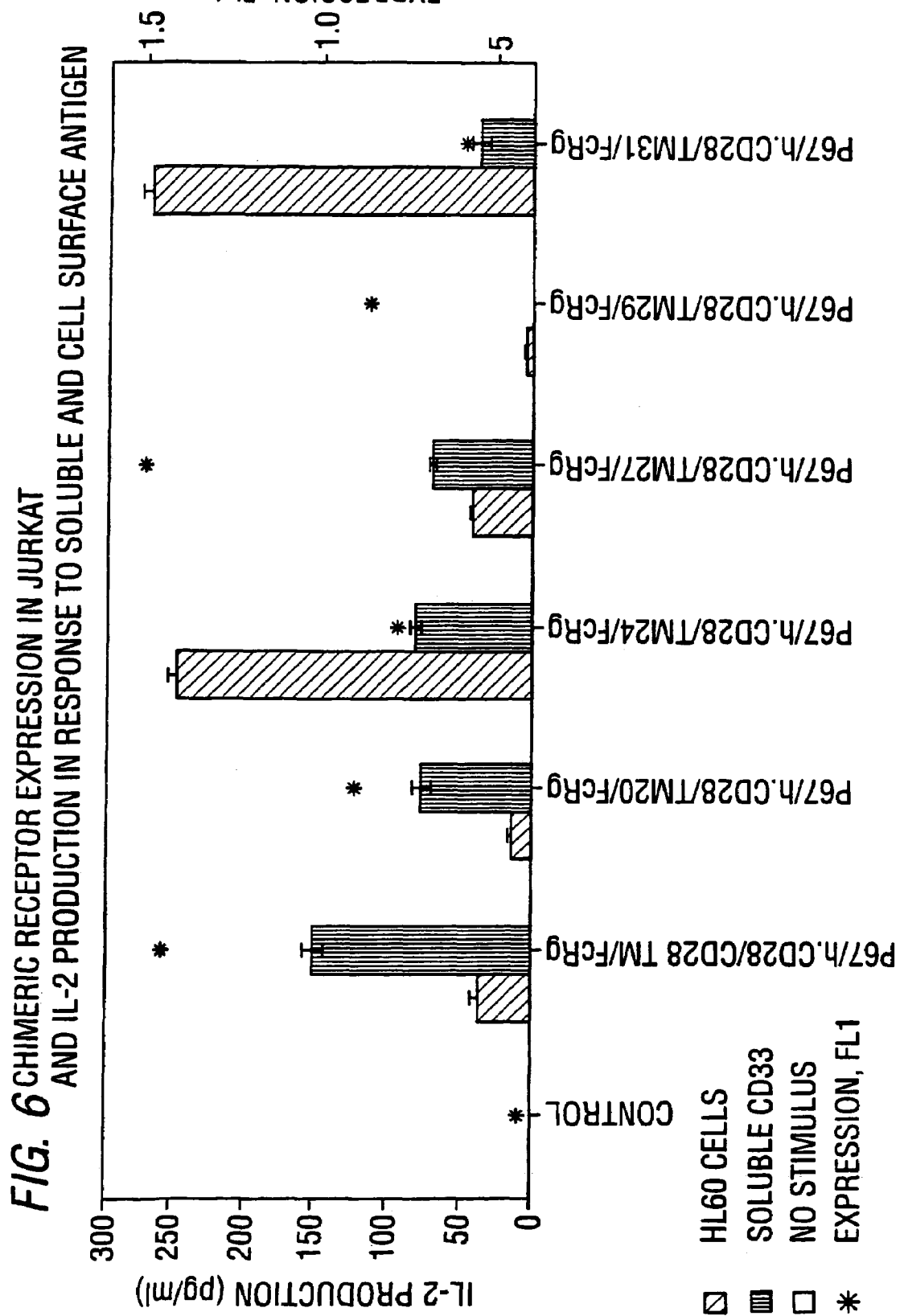

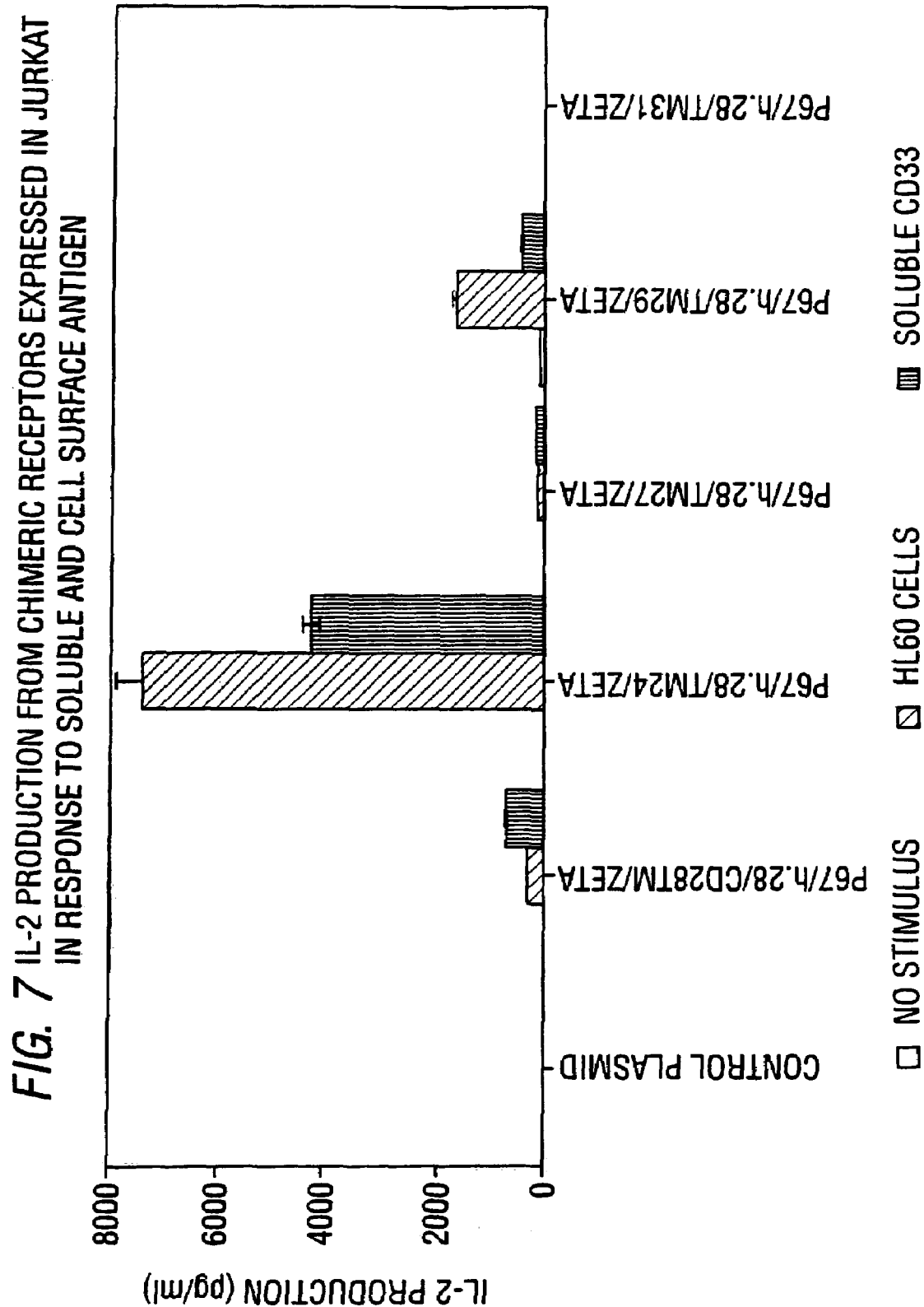
FIG. 7 IL-2 PRODUCTION FROM CHIMERIC RECEPTORS EXPRESSED IN JURKAT IN RESPONSE TO SOLUBLE AND CELL SURFACE ANTIGEN

SYNTHETIC TRANSMEMBRANE COMPONENTS

This application is a U.S. National Stage Application of PCT Application No. PCT/GB00/01476, filed Apr. 17, 2000.

The present invention relates to nucleic acids encoding synthetic polypeptides, the use of these polypeptides as discrete domains within a chimeric protein and to the use of such chimeric proteins in medicine and research.

The number of industrial and medical applications involving protein products and/or targets has increased considerably over recent years. This has resulted in a corresponding increase in the use of protein engineering to improve the existing (or to create novel) structural or functional characteristics of a protein.

In order to produce a successfully engineered protein, the changes that are introduced must be compatible with each other and the remaining structural and functional features of the protein. Although this process can be facilitated by knowledge of the three-dimensional structure, or by rational design based on predicted molecular models of the protein, success is not guaranteed and is difficult to achieve. Thus the de novo design of an entire protein or of an individual sub-unit or domain of a protein is still remarkably rare.

Receptor proteins normally consist of more than one domain and exist in a number of different forms. For example, they may be soluble proteins, they may be anchored or tethered to a membrane, or they may be true transmembrane proteins with domains either side of, and spanning, a membrane. The individual domains may play structural or functional roles within the receptor as a whole. The domains either may or may not be capable of functioning independently of any other domain. All of these considerations must be taken into account when engineering a receptor protein in order to alter its properties.

Functional chimeric receptor proteins (derived by the insertion or substitution of part of the sequence of one protein into another protein, so resulting in a hybrid protein with defined specificity for a ligand) have been designed. Binding of a ligand to the chimeric protein can result in the generation of an intracellular signal.

Examples of chimeric receptors are those that have been designed to target T-cells to other cells that express antigenic ligands on their surface.

In these receptors, ligand recognition is provided by an extracellular binding region of the molecule, in the same way that a naturally-occurring membrane binds to its target. Accordingly, when designing a chimeric receptor, a suitable extracellular binding region should be chosen which binds specifically to its target ligand with high affinity.

Binding of ligand to the chimeric receptor triggers a series of intracellular events leading to activation of the receptor-bearing cell. This activation is effected by the presence in the chimeric receptor molecule of an intracellular signalling domain. Activation of this domain may lead to a variety of biological effects within the cell, such as increased cellular proliferation, increased expression of cytokines with, for example, pro- or anti- inflammatory responses, stimulation of cytolytic activity, differentiation or other effector function, antibody secretion, phagocytosis, tumour infiltration and/or increased cellular adhesion.

Spacer domains have been used as additional structural components in chimeric receptors. They have been used to arrange the domains of the receptor in a desired conformation in order to optimise the binding or signalling potential of the receptor molecule. The inclusion of such spacers in the receptor may also facilitate the initial cloning steps when the nucleic acid elements encoding each domain of the protein are assembled.

The transmembrane component of a chimeric receptor protein and of membrane-associated proteins in general, typically serves to link the extracellular binding region of the protein to an intracellular cytoplasmic signalling region and thus to anchor the protein in the membrane of a cell. This component has conventionally been incorporated into a chimeric receptor as a natural part of either the intracellular signalling domain, the spacer domain, or the extracellular binding region, with which it is associated in the naturally occurring proteins from which these domains are derived.

A problem exists with the previously described chimeric receptor proteins in that they are susceptible to signalling not only in response to cell surface bound ligand, but also in response to the presence of soluble antigen. This is a particularly undesirable characteristic of a chimeric receptor and can limit the therapeutic potential of this approach (Eshar, Z. (1997) Cancer Immunol. Immunother. 45:131–136). Many antigens that would otherwise make attractive targets for chimeric receptor-based therapy are thus unsuitable because they are either shed from the surface of cells or they are secreted. They thus initiate systemic activation if bound by a chimeric receptor.

Specifically, many tumour-associated antigens, such as polymorphic epithelial mucin (PEM) and carcinoembryonic antigen (CEA), which are expressed on a wide range of solid tumours, are shed and are detectable in the serum at significant levels. The therapeutic use of chimeric receptors with specificity for this type of antigen ligand could be severely compromised by the presence of a circulating antigen component. This would not only lead to reduced efficacy but could potentially cause systemic toxicity due to the inappropriate release of cytokines.

An additional issue with chimeric receptors is presented by the poor understanding of the mechanisms by which these proteins convert the extracellular binding of ligand to receptor into intracellular signalling events. It is thought that these mechanisms involve clustering and association with endogenous cellular effector molecules. However, the relationship between the level of expression of a chimeric receptor protein and strength of intracellular signalling generated appears to vary between different systems. Therapeutic success in using chimeric proteins is likely to depend on carefully matching the level of expression of the protein to the level of expression of the particular target ligand, so that the appropriate degree of receptor cross-linking, clustering and oligomerisation can be achieved for optimal signalling.

The level of expression of proteins is generally controlled at the level of transcription. Thus, depending upon the level of expression of chimeric receptor protein that is required in the cell, a strong or weak promoter system is used. However, it is not possible to define precisely the level of receptor expression using such a method, since the efficacy of all promoter systems tends to vary between different cell types and under different physiological conditions. Furthermore, the use of strong promoter systems can be physiologically disruptive when used in vivo.

Accordingly, in order for the chimeric receptor approach to achieve its full therapeutic potential (in particular in cancer immunotherapy), ways must be found not only of allowing such receptors to distinguish between soluble and cell surface bound antigen, but also of tailoring their levels of expression.

SUMMARY OF THE INVENTION

We have found that the incorporation of a synthetic polypeptide as a transmembrane or membrane-anchoring domain in a membrane-associated protein, has totally unexpected effects on properties of that chimeric protein.

For example, the sensitivity of a chimeric receptor protein for antigen may be altered by incorporating a synthetic transmembrane region into the protein. We have also found that the sensitivity of intracellular signalling stimulated by the binding of antigen to an extracellular ligand-binding domain of the protein may be modified by effecting an appropriate choice of synthetic transmembrane domain. In addition, the specific inclusion of synthetic transmembrane components in a chimeric receptor molecule has an effect on modulating the response function of the chimeric receptor to different types of antigen. This allows the ratio of cell surface-associated antigen to soluble antigen that is bound by the receptor, and thus the response of the receptor to be precisely tailored.

Surprisingly, the level of expression of a membrane-associated protein is also affected by the incorporation of a synthetic transmembrane region. By selecting an appropriate synthetic transmembrane region, the level of expression of membrane-associated protein can be tailored as required.

The appropriate choice of synthetic transmembrane component may also be used to match the level of expression of the chimeric receptor to the level of expression of the particular target ligand for the receptor, so that the optimal degree of receptor cross-linking, clustering, oligomerisation and association with endogenous molecules can be achieved. This, in turn, optimises the activation of the signalling cascade within the cell in which the chimeric receptor is expressed. In this respect, specific synthetic transmembrane regions may be selected to optimise cross-linking of the receptor with other components of the membrane.

According to the present invention there is provided a nucleic acid encoding a membrane-associated protein that comprises a synthetic transmembrane region. For the avoidance of doubt, the term "synthetic" is used herein to mean "not naturally-occurring". As used herein, the term "transmembrane region" is defined as a predominantly hydrophobic sequence of amino acids that is capable of spanning a cell membrane.

The transmembrane region may be composed of one or more transmembrane domains, which may be the same or different. A transmembrane domain may in general be any oligo- or polypeptide which when folded under physiological conditions is of sufficient length to span the membrane of a cell. In general, this domain will be of between approximately 15 and approximately 35 amino acids in length, preferably 20–31 amino acids, enabling the domain to span a typical cell membrane, that is of the order of between approximately 2 and 6 nm in width.

The extremities of a transmembrane domain are defined by helix-breaker residues that disrupt the structure, such as, proline. Charged residues may also define the ends of the transmembrane domain, since these residues are energetically unstable in the hydrophobic environment of the membrane.

Suitable synthetic transmembrane regions comprise predominantly hydrophobic amino acids such as leucine and valine. Preferably, the synthetic transmembrane region comprises a sequence of amino acid residues of which at least 50%, more preferably at least 80%, are hydrophobic amino acid residues. In this respect, suitable amino acid residues include the hydrophobic residues Ala, Leu, Val, Ile, Pro, Phe or Met.

The synthetic transmembrane region may also be designed so as to possess an alpha helical structure, by constructing it from one or more alpha helix-promoting amino acid residues such as Ala, Asn, Cys, Gln, His, Leu, Met, Phe, Trp, Tyr or Val. Preferably, the hydrophobic alpha helix-promoting residues Ala, Met, Phe, Trp or Val are used. The hydrophobic alpha helix-promoting residues Phe, Trp or Val are preferred.

It has also been found preferable to include at each end of the transmembrane region the triplet phenylalanine, tryptophan, valine (Phe, Trp, Val, or in single letter code, FWV).

Examples of synthetic transmembrane regions are FWV (L)$_{14}$FWV (SEQ ID NO:21), FWV(L)$_{18}$FWV (SEQ ID NO:22), FWV(L)$_{21}$FWV (SEQ ID NO:23), FWV(L)$_{23}$FWV (SEQ ID NO:24), FWV(L)$_{25}$FWV (SEQ ID NO:25) (single letter amino acid code; see also FIG. 4). The components of choice as transmembrane regions are TM 20 (SEQ ID NO:21), TM 24 (SEQ ID NO:22), TM 27 (SEQ ID NO:23), TM 29 (SEQ ID NO:24), TM 31 (SEQ ID NO:25). As is clear from this Figure, the preferred synthetic sequences contain flanking "FWV" triplets, whilst the remainder of the sequence comprises a string of leucine residues. This sequence is predicted to form an α helical structure. Other protein structures capable of spanning a membrane (such as β sheet structures) may also be used.

The degree to which the level of expression of the protein has been altered by using the transmembrane region in accordance with the invention, can be assessed by a number of methods, as will be clear to the person of skill in the art. Particularly suitable methods are fluorescence-activated cell sorting (FACS) or Western blotting, using an antibody specific for the protein of interest and measurement of cytokine release in response to cell bound and/or soluble antigen.

The term "membrane-associated protein" as used herein is intended to mean any protein that contains one or more transmembrane domains. The protein may be, for example, a chimeric receptor comprising an extracellular ligand binding domain and at least one synthetic transmembrane domain linked to one or more intracellular signalling domains as described hereinafter. Alternatively, the membrane-associated protein may consist solely of one or more synthetic transmembrane domains linked to one or more intracellular domains as described below.

The protein to which the synthetic transmembrane region is linked in the membrane-associated protein may be derived from a protein that is naturally associated with the membrane, or it may be derived from a soluble protein. Examples of suitable soluble proteins include enzymes, enzyme inhibitors, enzyme substrates, peptide hormones, antigens, cytokines and immunoglobulins. Specific examples will be clear to the skilled man.

For membrane-associated proteins with more than one transmembrane domain, such as proteins of the tetraspan family, or the G-protein coupled receptor super-family (which have seven transmembrane domains), substitutions may be made of one or more transmembrane domains. For example, 1, 2, 3, or all 4 of the transmembrane domains in a tetraspan protein may be substituted by a synthetic transmembrane domain in order to alter a desired property of the protein.

An extracellular ligand binding domain may be present in the membrane-associated protein to define the required specificity of the protein for antigen. As used herein, the term "extracellular ligand binding domain" is intended to refer to any oligo- or polypeptide that is capable of binding to a ligand. Accordingly, this term is intended to include any binding domain of any molecule with affinity for ligand. The term thus includes antibody binding domains, antibody hypervariable loops and CDR domains, receptor binding domains and other ligand binding domains, examples of which will be readily apparent to those of skill in the art.

Preferably, the extracellular ligand binding domain is capable of interacting with a cell surface molecule. For example, this domain may be chosen to recognise a cell surface marker ligand expressed on target cells associated with a disease state such as viral, bacterial and parasitic infection, auto-immune disease, inflammation and cancer.

Examples of markers for cancer cells are the bombesin receptor expressed on lung tumour cells, CEA, PEM, CD33, Folate receptor, epithelial cell adhesion molecule (EPCAM) and erb-B2. Other molecules of choice are cell surface adhesion molecules, inflammatory cells present in auto-immune disease and T-cell receptors or antigens that give rise to autoimmunity. Further examples will be readily apparent to those of skill in the art.

In one aspect of the invention, the extracellular ligand binding domain may be chosen such that it interacts with one or more other extracellular ligand binding domains of other receptors. This aspect of chimeric receptor design is described in detail in co-pending co-owned patent application GB9809658.9 (Biological Products), the content of which is incorporated by reference herein in its entirety.

Membrane-associated proteins produced according to the method of the invention may provide multiply-associated domains that are capable of recognising a cell surface marker ligand expressed on a target cell. In this respect, particularly useful extracellular ligand binding domains include parts of receptors associated with binding two cell surface-associated molecules and especially include an antibody variable domain ($V_H$ or $V_L$), a T-cell receptor variable region domain (TCRα, TCRβ, TCRγ, TCRδ) or a CD8α, CD8β, CD11A, CD11B, CD11C, CD18, CD29, CD49A, CD49B, CD49C, CD49D, CD49E, CD49F, CD61, CD41 or CD51 chain. Of course, fragments of these domains or chains may be used where appropriate.

More than one extracellular ligand binding domain may be incorporated into the membrane-associated protein. Proteins which feature more than one extracellular ligand binding domain may, for example, recruit cellular immune effector cells such as T-cells, B-cells, NK-cells, macrophages, neutrophils, eosinophils, basophils or mast cells or components of the complement cascade. A particularly suitable combination of ligand specificities is anti-CD3 with anti-CD28, to specifically recruit and stimulate T-cells.

As will be clear to the skilled artisan, these combinations of extracellular ligand binding domains can be on separate polypeptide chains or may be in series on a single polypeptide chain.

It may also be desired for the extracellular ligand binding domains to be able to interact co-operatively with each other to form a ligand binding site. Particular examples include a $V_H$ domain paired with a $V_L$ domain, two or more TCRα, TCRβ, TCRγ and/or TCRδ domains, a CD8α or CD8β homo or heterodimer, CD18 paired with one or more of CD11a, b, or c, CD29 paired with one or more of CD49a, b, c, d, e or f and CD61 paired with CD41c and/or CD51. In this aspect of the invention, in binding to ligand, each extracellular ligand binding domain forms part of a ligand binding site and in doing so establishes a close spatial proximity of the chains which constitute the chimeric receptor.

In embodiments of the invention that involve co-operative interaction of chimeric receptor molecules, the synthetic transmembrane region may be designed so as to minimise its constitutive association with any domain of other chimeric or endogenous receptor molecules. Ideally, in these embodiments the transmembrane region will be designed to allow association of the receptor polypeptide chains only when ligand is bound by one or more of the extracellular domains. This preferable feature reduces undesirable random signal generation by ensuring that the intracellular signalling domains only interact when ligand is bound by the extra-cellular domain.

Where the membrane-associated protein produced according to the invention contains an extracellular ligand binding domain linked to one or more synthetic transmembrane domains, but lacks any intracellular signalling domains, such a protein may function as a recruitment receptor. A recruitment receptor is herein defined as a receptor that is expressed on the surface of a target cell, and that attracts effector cells to the target cell, either by virtue of its specificity for an immune receptor that is expressed on the surface of the effector cell, or by defining a marker that is diagnostic of disease so that immune effector cells are attracted to the site of disease. Once the immune system is activated or recruited, the normal function of the immune system takes over and the target cell may thus be destroyed. Preferred recruitment receptors are described in the Examples herein.

The membrane-associated proteins produced according to the invention may incorporate an intracellular signalling domain. As used herein, the term "intracellular signalling domain" is intended to mean any oligopeptide or polypeptide that can participate in the transduction of a signal which results in the direct or indirect activation of one or more intracellular messenger systems. Suitable intracellular messenger systems include, for example, kinase pathways such as those involving tyrosine kinase, protein kinase C or MAP kinase; G-protein or phospholipase-mediated pathways; calcium-mediated pathways; and pathways involving synthesis of a cytokine such as an interleukin e.g. IL-2, including NFAT and cAMP mediated pathways.

The intracellular signalling domain may be a naturally-occurring polypeptide signalling sequence or may be synthetic. Examples of suitable naturally-occurring sequences include sequences derived from: the T cell receptor, such as all or part of the zeta, eta or epsilon chain; CD28; CD4; CD8; the gamma chain of an Fc receptor or signalling components from a cytokine receptor, such as the interleukin, TNF or interferon receptors; a colony stimulating factor receptor e.g. GMCSF, tyrosine kinase e.g. ZAP-70, fyn, lck, Itk and syk; and binding domains thereof; an adhesion molecule e.g. LFA-1 and LFA-2; B29; MB-1; CD3 delta; CD3 gamma; CD5; or CD2.

Suitable synthetic intracellular signalling domains may contain peptide sequences that are similar to or are derived from any natural domain or portion thereof. As the skilled artisan will appreciate, amino acid mutations, deletions, insertions or substitutions may be made from natural sequences in order to modify the precise properties of the domains, in accordance with what is required for the membrane-associated protein. Examples of suitable synthetic signalling domains are given in co-pending United Kingdom patent application entitled "Synthetic signalling molecules", (Ref. PA451; PO21408WO) filed by Celltech Therapeutics Limited on even date herewith.

These signalling domains may be combined so as to allow the activation of a number of secondary messenger cascades through a single binding event. As will be clear to the skilled artisan, combinations of intracellular signalling domains can be on separate polypeptide chains or may be in series on a single polypeptide chain.

Between the extracellular ligand binding domain and transmembrane domain, or between the intracellular ligand binding domain and the transmembrane domain there may be incorporated a spacer domain. As used herein, the term "spacer domain" generally means any oligopeptide or polypeptide that functions to link the transmembrane domain to either of the extracellular ligand binding domains or intracellular signalling domains in the polypeptide chain. A spacer domain may comprise up to 300 amino acids, preferably 2 to 100 amino acids and most preferably 25 to 50 amino acids.

Spacer domains may be derived from all or part of naturally occurring molecules such as from all or part of the extracellular region of CD8, CD4 or CD28; all or part of an antibody constant region, including the hinge region; all or part of natural spacer components between the functional parts of intracellular signalling molecules, for example spacers between ITAMs (immunoglobulin tyrosine based activation motifs) may be used. Alternatively, the spacer may be a synthetic sequence that corresponds to a naturally occurring spacer sequence, or may be an entirely synthetic spacer sequence.

In one aspect of the invention, spacer domains may be incorporated into a membrane-associated protein that do not associate with one another. This aspect of receptor design is intended to minimise constitutive association of the membrane-associated proteins and so prevent constitutive activation of the molecules. Of course, the opposite effect may also be achieved if constitutive activation is desired. Either possibility may be achieved artificially by deleting, inserting, altering or otherwise modifying amino acids and naturally occurring sequences in the transmembrane and/or spacer domains which have sidechain residues that are capable of covalently or non-covalently interacting with the side chains of amino acids in other polypeptide chains. Particular examples of amino acids that can normally be predicted to promote association include cysteine residues, charged amino acids or amino acids such as serine or threonine within potential glycosylation sites.

According to a further aspect of the invention there is also provided a membrane-associated protein comprising an intracellular signalling domain and a synthetic transmembrane region.

Suitable candidate synthetic transmembrane regions are discussed in some detail above, as are suitable extracellular ligand binding domains, intracellular signalling domains and spacer domains. Preferably the extracellular ligand binding domain, spacer domain, and intracellular signalling domains of the membrane-associated proteins of the invention are derived from or are based on mammalian, most preferably human, sequences.

According to a still further aspect of the invention, there is provided a nucleic acid molecule encoding a membrane-associated protein according to any one of the above-described aspects of the invention. Preferably, the nucleic acid molecule comprises DNA.

Nucleic acid coding sequences for use in the invention are widely reported in the scientific literature and are also available in public databases. DNA may be commercially available, may be part of cDNA libraries or may be generated using standard molecular biology and/or chemistry procedures as will be clear to those of skill in the art. Particularly suitable techniques include the polymerase chain reaction (PCR), oligonucleotide-directed mutagenesis, oligonucleotide-directed synthesis techniques, enzymatic cleavage or enzymatic filling-in of gapped oligonucleotides. Such techniques are described by Maniatis et al in Molecular Cloning, Cold Spring Harbor Laboratory, New York 1989 and in the Examples contained herein.

The DNA of this aspect of the invention may be used with a carrier. The carrier may be a vector or other carrier suitable for introduction of the DNA ex-vivo or in-vivo into target cells and/or target host cells. Examples of suitable vectors include viral vectors such as retroviruses, adenoviruses, adeno-associated viruses (AAVs), Epstein-Barr virus (EBV) and Herpes simplex virus (HSV). Non-viral vectors may also be used, such as liposomal vectors and vectors based on DNA condensing agents such as the cationic lipids described in International patent applications nos. WO96/10038, WO97/18185, WO97/25329, WO97/30170 and WO97/31934. Where appropriate, the vector may additionally include promoter and regulatory sequences and/or replication functions from viruses such as retrovirus long terminal repeats (LTRs), AAV repeats, SV40 and human cytomegalovirus (hCMV) promoters and/or enhancers, splicing and polyadenylation signals and EBV and BK virus replication functions. Tissue-specific regulatory sequences such as the TCR-α promoter, E-selectin promoter and the CD2 promoter and locus control region may also be used. The carrier may be an antibody.

Each DNA molecule coding for a polypeptide chain of the chimeric receptor may be incorporated into a different carrier as described above. Preferably however, the DNA is incorporated into the same carrier. For this the DNA may be located for example on separate plasmids or may be advantageously part of a single plasmid additionally containing one or more promoter and/or regulatory sequences and/or replication functions as described above. The invention extends to a plasmid comprising DNA coding for a chimeric receptor according to the invention. Particularly useful plasmids of this type include the modified pBluescript SK+ (Stratagene) plasmid described in International patent application no. WO97/23613 and in the Examples contained herein.

The invention also includes cloning and expression vectors containing the DNA sequences of the above-described aspects of the invention. Such expression vectors will incorporate the appropriate transcriptional and translational control sequences, for example enhancer elements, promoter-operator regions, termination stop sequences, mRNA stability sequences, start and stop codons or ribosomal binding sites, linked in frame with the nucleic acid molecules of the invention.

Additionally, in the absence of a naturally-effective signal peptide in the protein sequence, it may be convenient to cause the recombinant protein to be secreted from certain hosts. Accordingly, further components of such vectors may include nucleic acid sequences encoding secretion signalling and processing sequences.

Vectors according to the invention include plasmids and viruses (including both bacteriophage and eukaryotic viruses). Many such vectors and expression systems are well known and documented in the art. Particularly suitable viral vectors include baculovirus-, adenovirus- and vaccinia virus-based vectors.

The expression of heterologous polypeptides and polypeptide fragments in prokaryotic cells such as *E. coli* is well established in the art; see for example *Molecular Cloning: a Laboratory Manual:* 2nd edition, Sambrook et al., 1989, Cold Spring Harbor Laboratory Press or *DNA* cloning: a practical approach, Volume II: Expression systems, edited by D. M. Glover (IRL Press, 1995). Expression in eukaryotic cells, including plant cells, in culture is also an option available to those skilled in the art for the production of heterologous proteins; see for example O'Reilly et al., (1994) *Baculovirus expression vectors-a laboratory manual* (Oxford University Press) or *DNA cloning: a practical approach, Volume IV: Mammalian systems*, edited by D. M. Glover (IRL Press, 1995).

Suitable vectors can be chosen or constructed for expression of the membrane-associated proteins of the invention, containing the appropriate regulatory sequences, including promoter sequences, terminator sequences, polyadenylation sequences, enhancer sequences, marker genes and other sequences as appropriate. Vectors may be plasmids, viral e.g. bacteriophage, or phagemid, as appropriate. For further details see *Molecular Cloning: a Laboratory Manual*. Many known techniques and protocols for manipulation of nucleic acid, for example, in the preparation of nucleic acid constructs, mutagenesis, sequencing, introduction of DNA into cells and gene expression, and analysis of proteins, are described in detail in *Short Protocols in Molecular Biology*, Second Edition, Ausubel et al. eds., (John Wiley & Sons, 1992) or *Protein Engineering: A practical approach* (edited by A. R. Rees et al., IRL Press 1993). For example, in eukaryotic cells, the vectors of choice are virus-based.

A further aspect of the present invention provides a host cell containing a nucleic acid encoding a membrane-associated protein of the above-described aspects of the invention. A still further aspect provides a method comprising introducing such nucleic acid into a host cell or organism.

Suitable hosts include commonly used prokaryotic species, such as *E. coli*, or eukaryotic yeasts that can be made to express high levels of recombinant proteins and that can easily be grown in large quantities. Mammalian cell lines grown in vitro are also suitable, particularly when using virus-driven expression systems such as the baculovirus expression system which involves the use of insect cells as hosts. Compounds may also be expressed in vivo, for example in insect larvae, mammalian tissues or plant cells.

Introduction of nucleic acid may employ any available technique. In eukaryotic cells, suitable techniques may include calcium phosphate transfection, DEAE-Dextran, electroporation, liposome-mediated transfection or transduction using retrovirus or other viruses, such as vaccinia or, for insect cells, baculovirus.

In bacterial cells, suitable techniques may include calcium chloride transformation, electroporation or transfection using bacteriophage. Bacterial cells will be of particular use in the methods described above in which the aim of the method is to increase levels of expression of membrane-associated protein. For example, one of the above-described aspects involves the alteration of the level of expression of a membrane-associated protein by substituting a membrane-anchoring region in the membrane-associated protein for a synthetic transmembrane component. High expression levels are generally more easy to achieve in prokaryotic cells than in eukaryotic cells. Furthermore, these systems are simpler and may more easily be manipulated. However, the system of choice will depend upon the particular membrane-associated protein of interest. Other factors will also be relevant, for example, the degree to which it is important for the fidelity of post-translational modification to be retained.

Introduction of the nucleic acid may be followed by causing or allowing expression from the nucleic acid, e.g. by culturing host cells under conditions for expression of the gene.

In one embodiment, the nucleic acid of the invention may be integrated into the genome (e.g. chromosome) of the host cell. Integration may be promoted by inclusion of sequences that promote recombination with the genome, in accordance with standard techniques.

For ex vivo use, the nucleic acid of this aspect of the invention may be introduced into effector cells removed from the target host using methods well known in the art e.g. transfection, transduction, biolistics, protoplast fusion, calcium phosphate-precipitated DNA transformation, electroporation, cationic lipofection, or targeted liposomes. The effector cells are then reintroduced into the host using standard techniques. Examples of suitable effector cells for expression of the chimeric receptors of the invention include cells associated with the immune system such as lymphocytes e.g. cytotoxic T-lymphocytes, tumour infiltrating lymphocytes, natural killer cells, neutrophils, basophils or T-helper cells, dendritic cells, B-cells, haematopoietic stem cells, macrophages, monocytes or natural killer (NK) cells. The use of cytotoxic T-lymphocytes is especially preferred.

The nucleic acid according to this aspect of the invention is particularly suitable for in vivo administration. The DNA may be in the form of a targeted carrier system in which a carrier as described above is capable of directing the DNA to a desired effector cell. Examples of suitable targeted delivery systems include targeted naked DNA, targeted liposomes encapsulating and/or complexed with the DNA, targeted retroviral systems and targeted condensed DNA such as protamine and polylysine-condensed DNA.

Targeting systems are well known in the art and include, for example, using antibodies or fragments thereof against cell surface antigens expressed on target cells in vivo such as CD8; CD16; CD4; CD3; selectins e.g. E-selectin; CD5; CD7; CD34; and activation antigens e.g. CD69 and IL-2R. Alternatively, other receptor-ligand interactions can be used for targeting e.g. CD4 to target $HIV_{gp}160$-expressing target cells.

In general, the use of antibody-targeted DNA is preferred, particularly antibody-targeted naked DNA, antibody-targeted condensed DNA and especially antibody-targeted liposomes. Types of liposomes that may be used include, for example, pH-sensitive liposomes where linkers cleaved at low pH may be used to link the antibody to the liposome. Cationic liposomes that fuse with the cell membrane and deliver the recombinant chimeric receptor DNA according to this aspect of the invention directly into the cytoplasm may also be used. Liposomes for use in the invention may also have hydrophilic molecules, for example, polyethylene glycol polymers attached to their surface to increase their circulating half-life. There are many examples in the art of suitable groups for attaching to liposomes or other carriers; see for example International patent applications nos. WO88/04924, WO90/09782, WO91/05545, WO91/05546, WO93/19738, WO94/20073 and WO94/22429. The antibody or other targeting molecule may be linked to the DNA, condensed DNA or liposome using conventional readily available linking groups and reactive functional groups in the antibody, e.g. thiols or amines, and in the DNA or DNA-containing materials.

Non-targeted carrier systems may also be used and in these systems, targeted expression of the DNA is advantageous. Targeted expression of the DNA may be achieved for example by using T-cell specific promoter systems such as the zeta promoter and CD2 promoter and locus control region, CD4, CD8, TCRα and TCRβ promoters, cytokine promoters such as the IL2 promoter and the perforin promoter.

The DNA according to this aspect of the invention may be used ex vivo and in a further aspect of the invention, effector cells that have been transfected with DNA according to this aspect of the invention are provided. The effector cells may be any of those described above which are suitable for ex vivo use and are preferably T-cells, most preferably cytotoxic T-cells.

According to a further aspect of the invention there is provided a composition comprising a membrane-associated protein according to the above-described aspects of the invention or a nucleic acid molecule coding therefor, in conjunction with a pharmaceutically-acceptable excipient.

Suitable excipients will be well known to those of skill in the art and may, for example, comprise a phosphate-buffered saline (0.01M phosphate salts, 0.138M NaCl, 0.0027M KC, pH7.4), a liquid such as water, saline, glycerol or ethanol, optionally also containing mineral acid salts such as hydrochlorides, hydrobromides, phosphates, sulphates and the like; and the salts of organic acids such as acetates, propionates, malonates, benzoates and the like. Auxiliary substances such as wetting or emulsifying agents and pH buffering substances, may also be present. A thorough discussion of pharmaceutically acceptable excipients is available in Remington's Pharmaceutical Sciences (Mack Pub. Co., N.J. 1991). Preferably, the compositions will be in a form suitable for parenteral administration e.g. by injection or infusion, for example by bolus injection or continuous infusion or particle-mediated injection. Where the composition is for injection or infusion, it may take the form of a suspension, solution or emulsion in an oily or aqueous vehicle and it may contain formulatory agents such as suspending, preservative, stabilising and/or dispersing agents. Alternatively, the composition may be in dry form, for reconstitution before use with an appropriate sterile liquid. For particle-mediated administration the DNA may be coated on particles such as microscopic gold particles.

A carrier may also be used that does not itself induce the production of antibodies harmful to the individual receiving the composition and which may be administered without undue toxicity. Suitable carriers are typically large, slowly metabolised macromolecules such as proteins, polysaccharides, polylactic acids, polyglycolic acids, polymeric amino acids, amino acid copolymers and inactive virus particles. Pharmaceutical compositions may also contain preservatives to ensure a long shelf life in storage.

If the composition is suitable for oral administration the formulation may contain, in addition to the active ingredient, additives such as: starch (for example potato, maize or wheat starch or cellulose), starch derivatives such as microcrystalline cellulose, silica, various sugars such as lactose, magnesium carbonate and/or calcium phosphate. It is desirable that, if the formulation is for oral administration it will be well tolerated by the patient's digestive system. To this end, it may be desirable to include in the formulation mucus formers and resins. It may also be desirable to improve tolerance by formulating the compositions in a capsule that is insoluble in the gastric juices. It may also be preferable to include the composition in a controlled release formulation.

The membrane-associated proteins of the invention and nucleic acids coding therefor are of use in medicine. According to a further aspect of the invention there is provided a method of treatment of a human or animal subject, the method comprising administering to the subject an effective amount of: a membrane-associated protein according to the above-described aspects of the invention; a DNA delivery system as described above; or transfected effector cells, in a therapeutically-effective amount.

The exact amount of active composition to be used will depend on the age and condition of the patient, the nature of the disease or disorder and the route of administration, but may be determined using conventional means, for example by extrapolation of data derived from animal experiments. In particular, for ex vivo use the number of transfected effector cells required may be established by ex vivo transfection and reintroduction into an animal model of a range of effector cell numbers.

Similarly the quantity of DNA required for in vivo use may be established in animals using a range of DNA concentrations.

The present invention may be useful in the treatment of a number of diseases or disorders. Such diseases or disorders may include those described under the general headings of infectious diseases, e.g. HIV infection; inflammatory disease/autoimmunity e.g. rheumatoid arthritis, osteoarthritis, inflammatory bowel disease; cancer; allergic/atopic diseases e.g. asthma, eczema; congenital e.g. cystic fibrosis, sickle cell anaemia; dermatologic, e.g. psoriasis; neurologic, e.g. multiple sclerosis; transplants e.g. organ transplant rejection, graft-versus-host disease; metabolic/idiopathic disease e.g. diabetes.

According to a yet further aspect, the present invention provides for the use of a membrane-associated protein according to the above-referenced aspects of the invention, a nucleic acid encoding such a protein or a pharmaceutical composition comprising either or both of these agents in therapy.

According to a still further aspect of the invention there is provided the use of membrane-associated protein according to the above-referenced aspects of the invention or a nucleic acid encoding therefor, in the manufacture of a medicament for the treatment or prevention of a disease in a mammal, preferably a human.

Transgenic animals transformed so as to express or over-express in the germ line one or more membrane-associated proteins as described herein form a still further aspect of the invention, along with methods for their production. Many techniques now exist to introduce transgenes into the embryo or germ line of an organism, such as for example, illustrated in Watson et al., (1994) *Recombinant DNA* (2nd edition), Scientific American Books. Preferred host animals are rodents.

Various aspects and embodiments of the present invention will now be described in more detail by way of example. It will be appreciated that modification of detail may be made without departing from the scope of the invention.

All documents mentioned in the text are incorporated herein by reference.

BRIEF DESCRIPTION OF THE FIGURES

FIG. 2: Sequence of signalling component cassette, including the sense strand (SEQ ID NO:1) and the antisense strand (SEQ ID NO:2).

FIG. 3: Oligonucleotide sequences for chimeric receptor construction, including oligonucleotides S0146 (SEQ ID NO:3), A6081 (SEQ ID NO:4), A6082 (SEQ ID NO:5), A6083 (SEQ ID NO:6), A9515 (SEQ ID NO:7), A9516 (SEQ ID NO:8), B6463 (SEQ ID NO:9), B6464 (SEQ ID NO:10), B6465 (SEQ ID NO:11), B6466 (SEQ ID NO:12), B6467 (SEQ ID NO:13), B6468 (SEQ ID NO:14), B6469 (SEQ ID NO:15), B6470 (SEQ ID NO:16), B6471 (SEQ ID NO:17), B6472 (SEQ ID NO:18), C3208 (SEQ ID NO:19), and C3209 (SEQ ID NO:20).

FIG. 4: Sequence of synthetic transmembrane components, including TM20 (SEQ ID NO:21), TM24 (SEQ ID NO:22), TM27 (SEQ ID NO:23), TM29 (SEQ ID NO:24), and TM31 (SEQ ID NO:25).

FIG. 5: Expression in Cos cells of recruitment receptors with different synthetic transmembrane regions.

FIG. 6: Chimeric receptor expression in Jurkat cells and IL-2 production in response to solid phase and cell surface antigen.

FIG. 7: Chimeric receptor expression in Jurkat cells and IL-2 production in response to solid phase and cell surface antigen.

EXAMPLES

Example 1

Construction of Cloning Cassette System

Figure 1:
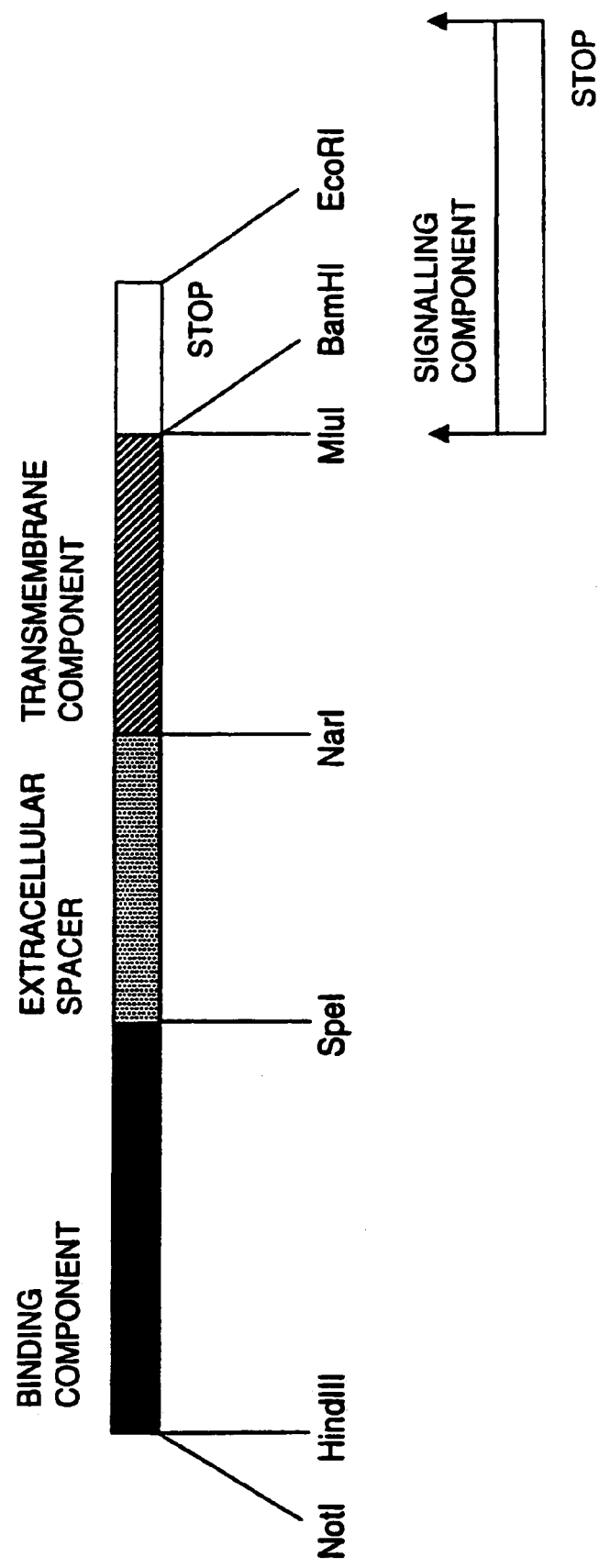
FIG. 1: Cloning cassette for chimeric receptor construction.

To facilitate construction of chimeric receptors with different binding, extracellular spacer, transmembrane and signalling components, a cloning cassette system was devised in pBluescript SK+ (Stratagene). This is a modification of our cassette system described in International Patent Specification No. WO97/23613.

This new cassette system is shown in FIG. 1. The binding component has 5' Not I and Hind III restriction sites and a 3' Spe I restriction site. The extracellular spacer has a 5' Spe I site (Thr, Ser) and a 3' Nar I site (Gly, Ala). The transmembrane component has a 5' Nar I site (Gly, Ala) and 3' Mlu I (Thr, Arg) and BamHI sites (Gly, Ser). The signalling component has a 5' BamHI site and a 3' EcoRI site. In between this BamHI and EcoRI site is a stop codon for receptors without a signalling component.

To generate this cassette, a 200 bp fragment was PCR assembled using oligos:—S0146 (SEQ ID NO:3), A6081 (SEQ ID NO:4), A6082 (SEQ ID NO:5) and A6083 (SEQ ID NO:6) (FIG. 3). This fragment starts with a SpeI site and consists of the extracellular spacer h.CD28, the human CD28 transmembrane region, a stop codon and finishes with an EcoRI site (SEQ ID NO:1) (see FIG. 2). This PCR fragment was then restricted with SpeI and EcoRI and substituted for the same fragment in our previously described cloning cassette system to join the binding component (International Patent WO97/23613; FIG. 2).

Example 2

Construction of Chimeric Receptors With Different Transmembrane Components a) P67scFv/h.CD28/CD28Tm/FcRγChimeric Receptor This construct was generated from the cassette described above and forms the basis for chimeric receptor constructs (b) to (f). The FcRγ intracellular component was PCR cloned with oligos A9515 (SEQ ID NO:7) and A9516 (SEQ ID NO:8) (FIG. 3) from human Leukocyte cDNA (Clontech) and cloned into the BamHI site of the described cassette (FIG. 1).

The binding component, P67 single chain Fv (scFv) with specificity for CD33 and CD33 on HL60 cells, consists of a human antibody leader sequence and the variable component of the light chain of the engineered human antibody linked via a (Gly$_4$Ser)$_5$ (SEQ ID NO:26) linker to the variable component of the heavy chain of the engineered human antibody. This binding component is described in WO 97/23613. The extracellular spacer component h.CD28, consists of residues 234 to 243 of human IgG1 hinge and residues 118 to 134 of human CD28. The transmembrane component consists of residues 135 to 161 of human CD28 (A. Aruffo & B. Seed 1987 PNAS 84 8573–8577). The intracellular component consists of residues 27 to 68 of the γ chain of human FcεR1 (Kuster et al (1990) J. Biol. Chem. 265, 6448–6452).

b) P67scFv/h.CD28/Tm20/FcRγ Chimeric Receptor

This chimeric receptor is the same as in 2 (a) above, except that the transmembrane component consists of 20 synthetic amino acid residues (SEQ ID NO:21) (FIG. 4). This transmembrane component was constructed by annealing oligos B6471 (SEQ ID NO:17) and B6472 (SEQ ID NO:18) (FIG. 3) which are designed so that a 5' overhang forms a NarI site and a 3' overhang forms a BamHI site. These annealed oligos were then substituted for the CD28 transmembrane in construct 2 (a) on a NarI to BamHI fragment.

c) P67scFv/h.CD28/Tm24/FcRγ Chimeric Receptor

This chimeric receptor is the same as in 2 (a) above except that the transmembrane component consists of 24 synthetic amino acid residues (SEQ ID NO:22) (FIG. 4). This transmembrane component was constructed by annealing oligos B6469 (SEQ ID NO:15) and B6470 (SEQ ID NO:16) (FIG. 3) which are designed so that a 5' overhang forms a NarI site and a 3' overhang forms a BamHI site. These annealed oligos were then substituted for the CD28 transmembrane in construct 2 (a) on a NarI to BamHI fragment.

d) P67scFv/h.CD28/Tm27/FcRγ Chimeric Receptor

This chimeric receptor is the same as in 2 (a) above except that the transmembrane component consists of 27 synthetic amino acid residues (SEQ ID NO:23) (FIG. 4). This transmembrane component was constructed by annealing oligos B6467 (SEQ ID NO:13) and B6468 (SEQ ID NO:14) (FIG. 3) which are designed so that a 5' overhang forms a NarI site and a 3' overhang forms a BamHI site. These annealed oligos were then substituted for the CD28 transmembrane in construct 2 (a) on a NarI to a BamHI fragment.

e) P67scFv/h.CD28/Tm29/FcRγ Chimeric Receptor

This chimeric receptor is the same as in 2 (a) above except that the transmembrane component consists of 29 synthetic amino acid residues (SEQ ID NO:24) (FIG. 4). This transmembrane component was constructed by annealing oligos B6465 (SEQ ID NO:11) and B6466 (SEQ ID NO:12) (FIG. 3) which are designed so that a 5' overhang forms a NarI site and a 3' overhang forms a BamHI site. These annealed oligos were then substituted for the CD28 transmembrane in construct 2 (a) on a NarI to BamHI fragment.

f) P67scFv/h.CD28/Tm31/FcRγ Chimeric Receptor

This chimeric receptor is the same as in 2 (a) above except that the transmembrane component consists of 31 synthetic amino acid residues (SEQ ID NO:25) (FIG. 4). This transmembrane component was constructed by annealing oligos B6463 (SEQ ID NO:9) and B6464 (SEQ ID NO:10) (FIG. 3) which are designed so that 5' overhang forms a NarI site and a 3' overhang forms a BamHI site. These annealed oligos were then substituted for the CD28 transmembrane in construct 2 (a) on a NarI to BamHI fragment.

g) P67scFv/h.CD28/CD28Tm/TCRζ Recruitment Receptor

This construct was generated from the cassette described above and forms the basis for chimeric receptor constructs 2 (h) to 2 (k). The TCRζ intracellular component was PCR cloned with oligos C3208 (SEQ ID NO:19) and C3209 (SEQ ID NO:20) (FIG. 3) from human Leukocyte cDNA (Clonetech). This PCR fragment was restricted with Mlu I and EcoR I and substituted for this fragment in the described cassette (FIG. 1).

The binding component, P67 single chain Fv (scFv) consists of a human antibody leader sequence and the variable component of the light chain of the engineered human antibody linked via a (Gly$_4$Ser)$_5$ (SEQ ID NO:26) linker to the variable component of the heavy chain of the engineered human antibody. This binding component is described in WO 97/23613. The extracellular spacer component h.CD28, consists of residues 234 to 243 of human IgG1 hinge and residues 118 to 134 of human CD28. The transmembrane component consists of residues 135 to 161 of human CD28 (A. Aruffo & B. Seed 1987 PNAS 84 8573–8577). The intracellular component consists of residues 31 to 142 of human TCRζ chain (Weissman et al: PNAS 85, 9709–9713, 1988. Moingeon et al: Eur. J. Immunol. 20, 1741–1745, 1990.)

h) P67scFv/h.CD28/Tm24/TCRζ Chimeric Receptor

This chimeric receptor is the same as 2 (g) except that the transmembrane component consists of 24 synthetic amino acid residues (SEQ ID NO:22) (FIG. 4). This construct was generated by substituting a SpeI to Mlu I fragment from chimeric receptor 2 (c) for the same fragment in chimeric receptor 2 (g).

i) P67scFv/h.CD28/Tm27/TCRζ Chimeric Receptor

This chimeric receptor is the same as in 2 (g) above except that the transmembrane component consists of 27 synthetic amino acid residues (SEQ ID NO:23) (FIG. 4). This construct was generated by substituting a SpeI to Mlu I fragment from chimeric receptor 2 (d) for the same fragment in chimeric receptor 2 (g).

j) P67scFv/h.CD28/Tm29/TCRζ Chimeric Receptor

This chimeric receptor is the same as in 2 (g) above except that the transmembrane component consists of 29 synthetic amino acid residues (SEQ ID NO:24) (FIG. 4). This construct was generated by substituting a SpeI to Mlu I fragment from chimeric receptor 2 (e) for the same fragment in chimeric receptor 2 (g).

k) P67scFv/h.CD28/Tm31/TCRζ Chimeric Receptor

This chimeric receptor is the same as in 2 (g) above except that the transmembrane component consists of 31 synthetic amino acid residues (SEQ ID NO:25) (FIG. 4). This construct was generated by substituting a SpeI to Mlu I fragment from chimeric receptor 2 (f) for the same fragment in chimeric receptor 2 (g).

Example 3

Construction of Recruitment Receptors With Different Transmembrane Components a) P67scFv/h.CD28/CD28Tm.stop Recruitment Receptor This construct was generated as described for the cloning cassette and forms the basis for subsequent recruitment receptor constructs (FIGS. 1 and 2).

The binding component, P67 single chain Fv (scFv) consists of a human antibody leader sequence and the variable component of the light chain of the engineered human antibody linked via a (Gly$_4$Ser)$_5$ (SEQ ID NO:26) linker to the variable component of the heavy chain of the engineered human antibody. This binding component is described in WO 97/23613. The extracellular spacer component h.CD28, consists of residues 234 to 243 of human IgG1 hinge and residues 118 to 134 of human CD28. The transmembrane component consists of residues 135 to 161 of human CD28 (A. Aruffo & B. Seed 1987 PNAS84 8573–8577). This is followed by an in frame stop codon.

b) P67scFv/h.CD28/Tm20.stop Recruitment Receptor

This recruitment receptor is the same as in 3 (a) above except that the transmembrane component consists of 20 synthetic amino acid residues (SEQ ID NO:21) (FIG. 4). This construct was generated by substituting a SpeI to Mlu I fragment from chimeric receptor 2 (b) for the same fragment in recruitment receptor 3 (a).

c) P67scFv/h.CD28/Tm24.stop Recruitment Receptor

This recruitment receptor is the same as in 3 (a) above except that the transmembrane component consists of 24 synthetic amino acid residues (SEQ ID NO:22) (FIG. 4). This construct was generated by substituting a SpeI to Mlu I fragment from chimeric receptor 2 (c) for the same fragment in recruitment receptor 3 (a).

d) P67scFv/h.CD28/Tm27.stop Recruitment Receptor

This recruitment receptor is the same as in 3 (a) above except that the transmembrane component consists of 27 synthetic amino acid residues (SEQ ID NO:23) (FIG. 4). This construct was generated by substituting a SpeI to Mlu I fragment from chimeric receptor 2 (d) for the same fragment in recruitment receptor 3 (a).

e) P67scFv/h.CD28/Tm29.stop Recruitment Receptor

This recruitment receptor is the same as in 3 (a) above except that the transmembrane component consists of 29 synthetic amino acid residues (SEQ ID NO:24) (FIG. 4). This construct was generated by substituting a SpeI to Mlu I fragment from chimeric receptor 2 (e) for the same fragment in recruitment receptor 3 (a).

f) P67scFv/h.CD28/Tm31.stop Recruitment Receptor

This recruitment receptor is the same as in 3 (a) above except that the transmembrane component consists of 31 synthetic amino acid residues (SEQ ID NO:25) (FIG. 4). This construct was generated by substituting a SpeI to Mlu I fragment from chimeric receptor 2 (f) for the same fragment in recruitment receptor 3 (a).

Example 4

Analysis of Receptors a) Construction of Expression Plasmids

The chimeric receptor constructs were subcloned from pBluescript KS+ into the expression vector pEE6hCMV.ne (C. R. Bebbington (1991), Methods 2, 136–145) on a HindIII to EcoRI restriction fragment. The expression vector with no chimeric receptor genes is used as a negative control in subsequent experiments.

b) Stable Transfection into Jurkat E6.1 Cells

The expression plasmids were linearised and transfected into Jurkat E6.1 cells (ECACC) by electroporation using a Bio-rad Gene Pulser. 10 μg of DNA per $2.5 \times 10^6$ cells were given two pulses of 1000 V, 3 μF in 1 ml PBS. Cells were left to recover overnight in non-selective media before being selected and cultured in media supplemented with the antibiotic G418 (Sigma) at 1.5 mg/ml. After approximately four weeks cells were ready for analysis.

c) Transient Transfection into Cos-1 Cells

Sub-confluent 6 well plates were transfected by coating with 15 μg of expression plasmid DNA complexed with DEAE/DEXTRAN at a final concentration of 0.4 mg/ml for 3 hours at 37° C./8% $CO_2$ and then shocking with 10% DMSO. Cells were analysed three days later.

d) FACS Analysis of Surface Expression

For both Jurkat and Cos-1 cells approximately $5 \times 10^5$ cells were stained with 1 μg/ml FITC labelled antigen, CD33. Fluorescence was analysed by a FACScan cytometer (Becton Dickinson).

e) IL-2 Production Analysis of Function $2 \times 10^5$ cells were incubated at 37° C./8% $CO_2$ for 20 hours in 96 well plates with soluble CD33 at 5 μg/ml or HL60 target cells at an effector: target ratio of 1:1 or in 96 well plates (Nunc Immunol) pre-coated with soluble CD33 at 5 μg/ml. Cell supernatants were then harvested and assayed for human IL-2 (R & D Systems Quantikine kit).

Example 5

Results

The substitution of a non naturally-occurring transmembrane component for the CD28 transmembrane domain enabled expression of chimeric receptors in Jurkat (FIG. 6) and recruitment molecules in Cos-1 cells (FIG. 5). Use of the transmembrane component TM27 (SEQ ID NO:23) conferred expression of chimeric receptors in Jurkat equivalent to that seen with the naturally occurring CD28 transmembrane domain. TM31 (SEQ ID NO:25) led to relatively low expression of the chimeric receptor in Jurkat; intermediate levels of expression were seen with TM20 (SEQ ID NO:21), TM24 (SEQ ID NO:22) and TM29 (SEQ ID NO:24).

Choice of synthetic transmembrane component was found to influence the response of chimeric receptors to antigen.

The FcRγ signalling component in the chimeric receptor described, when coupled to a CD28 transmembrane domain, demonstrated a marked preference for soluble rather than cell surface-expressed antigen. Substitution of just the transmembrane domain for either TM24 (SEQ ID NO:22) or TM31 (SEQ ID NO:25) led to a dramatic change in antigen preference, with a greater that five fold increase in IL-2 production from cell surface-expressed antigen and an up to three fold decrease in IL-2 production from soluble antigen. The net effect of this was to convert a three fold deficit of IL-2 production from cell surface-expressed antigen with respect to soluble antigen into a five fold excess.

In constructs featuring synthetic transmembrane components linked to the zeta signalling component a similar antigen preference was observed. In this case substitution of the CD28 transmembrane region for either TM24 (SEQ ID NO:22) or TM29 (SEQ ID NO:24) led to an increase in IL-2 production in response to cell surface expressed antigen compared to soluble antigen. With TM24 (SEQ ID NO:22) the net effect was to convert a greater than two fold deficit of IL-2 production from cell surface-expressed antigen with respect to soluble antigen into a two fold excess (FIG. 7).

SUMMARY

Substitution of naturally-occurring transmembrane domains for synthetic sequences has shown the ability to alter function by reversing the preference of chimeric receptors to signal in response to soluble antigen over cell surface-expressed antigen.

Careful selection and design of the transmembrane domain of proteins will allow expression of the protein to be adjusted. In addition, where more than one protein is expressed, the relative amounts of each can be modulated by the choice of the transmembrane component.

The invention claimed is:

1. A nucleic acid encoding a chimeric receptor comprising
    an extracellular ligand binding domain comprising a binding domain derived from a $V_H$ or $V_L$ antibody variable domain; a TCRα, TCRβ, TCRγ, or TRCδ T-cell receptor variable region domain: or a CD8α, CD8β, CD11A, CD11B, CD11C, CD18, CD29, CD49A, CD49B, CD49C, CD49D, CD49E, CD49F, CD61, CD41, or CD51 chain,
    an extracellular spacer domain,
    a synthetic transmembrane domain comprising TM24 (SEQ ID NO:22),
    and an intracellular signaling domain comprising a signaling domain derived from the zeta, eta, or epsilon chain of the T-cell receptor: CD28; CD4; CD8; the gamma chain of the Fc receptor; or a signaling component from an interleukin, TNF, or interferon receptor, or from GMCSF, ZAP-70, fyn, lck, Itk, syk, LFA-1, LFA-2, B29, MB-1, CD3δ, CD3γ, CD5, or CD2.

2. A nucleic acid according to claim 1, wherein the intracellular signaling domain is synthetic.

3. A vector comprising a nucleic acid according to claim 1.

4. A chimeric receptor encoded by a nucleic acid according to claim 1.

5. An isolated host cell comprising a nucleic acid according to claim 1.

6. A composition comprising a nucleic acid according to claim 1 in conjunction with a pharmaceutically acceptable excipient.

7. A composition comprising a vector according to claim 3 in conjunction with a pharmaceutically acceptable excipient.

8. A composition comprising a chimeric receptor according to claim 4 in conjunction with a pharmaceutically acceptable excipient.

9. An isolated host cell comprising a vector according to claim 3.

10. An isolated host cell comprising a chimeric receptor according to claim 4.

* * * * *

SEQUENCE LISTING

```
<160> NUMBER OF SEQ ID NOS: 26

<210> SEQ ID NO 1
<211> LENGTH: 200
<212> TYPE: DNA
<213> ORGANISM: Artificial Sequence
<220> FEATURE:
<223> OTHER INFORMATION: PCR Fragment Figure 2 (top)

<400> SEQUENCE: 1
cgactagtga caaaactcac acatgcccac cgtgcccaaa agggaaacac ctttgtccaa      60
gtcccctatt tcccggacct tctaagcccg gcgccttttg ggtgctggtg gtggttggtg     120
gagtcctggc ttgctatagc ttgctagtaa cagtggcctt tattattttc tgggtgacgc     180
gtggatcctg agaattcata                                                 200

<210> SEQ ID NO 2
<211> LENGTH: 200
<212> TYPE: DNA
<213> ORGANISM: Artificial Sequence
<220> FEATURE:
<223> OTHER INFORMATION: PCR Fragment Figure 2 (bottom)

<400> SEQUENCE: 2
```

```
gctgatcact gttttgagtg tgtacgggtg gcacgggttt tcccttttgtg gaaacaggtt    60 cagggataa agggcctgga agattcgggc cgcggaaaac ccacgaccac caccaaccac      120
ctcaggaccg aacgatatcg aacgatcatt gtcaccggaa ataataaaag acccactgcg    180
cacctaggac tcttaagtat                                                 200

<210> SEQ ID NO 3
<211> LENGTH: 65
<212> TYPE: DNA
<213> ORGANISM: Artificial Sequence
<220> FEATURE:
<223> OTHER INFORMATION: S0146

<400> SEQUENCE: 3
cgactagtga caaaactcac acatgcccac cgtgcccaaa agggaaacac ctttgtccaa    60
ctccc                                                                 65

<210> SEQ ID NO 4
<211> LENGTH: 63
<212> TYPE: DNA
<213> ORGANISM: Artificial Sequence
<220> FEATURE:
<223> OTHER INFORMATION: A6081

<400> SEQUENCE: 4 gcctttttggg tgctggtggt ggttggtgga gtcctggctt gctatagctt gctagtaaca   60
gtg                                                                   63

<210> SEQ ID NO 5
<211> LENGTH: 67
<212> TYPE: DNA
<213> ORGANISM: Artificial Sequence
<220> FEATURE:
<223> OTHER INFORMATION: A6082

<400> SEQUENCE: 5
tatgaattct caggatccac gcgtcaccca gaaaataata aaggccactg ttactagcaa    60
gctatag                                                               67

<210> SEQ ID NO 6
<211> LENGTH: 59
<212> TYPE: DNA
<213> ORGANISM: Artificial Sequence
<220> FEATURE:
<223> OTHER INFORMATION: A6083

<400> SEQUENCE: 6
caccaccagc acccaaaagg cgccgggctt agaaggtccg ggaaataggg gacttggac      59

<210> SEQ ID NO 7
<211> LENGTH: 29
<212> TYPE: DNA
<213> ORGANISM: Artificial Sequence
<220> FEATURE:
<223> OTHER INFORMATION: A9515

<400> SEQUENCE: 7
ggctgatcac gactgaagat ccaagtgcg                                       29

<210> SEQ ID NO 8
<211> LENGTH: 36
<212> TYPE: DNA
<213> ORGANISM: Artificial Sequence
```

<220> FEATURE:
<223> OTHER INFORMATION: A9516

<400> SEQUENCE: 8
tatgaattct caggatccct gtggtggttt ctcatg         36

<210> SEQ ID NO 9
<211> LENGTH: 98
<212> TYPE: DNA
<213> ORGANISM: Artificial Sequence
<220> FEATURE:
<223> OTHER INFORMATION: B6463

<400> SEQUENCE: 9
cgccttttgg gtgctgctgc tcctgctgct cctgctcctg ctgctcctgc tgctgctcct    60
gctactgctc ctgctgctcc tgctgctctt ctgggtga                            98

<210> SEQ ID NO 10
<211> LENGTH: 100
<212> TYPE: DNA
<213> ORGANISM: Artificial Sequence
<220> FEATURE:
<223> OTHER INFORMATION: B6464

<400> SEQUENCE: 10
cgcgtcaccc agaagagcag caggagcagc aggagcagta gcaggagcag cagcaggagc    60
agcaggagca ggagcagcag gagcagcagc acccaaaagg                          100

<210> SEQ ID NO 11
<211> LENGTH: 92
<212> TYPE: DNA
<213> ORGANISM: Artificial Sequence
<220> FEATURE:
<223> OTHER INFORMATION: B6465

<400> SEQUENCE: 11
cgccttttgg gtgctgctgc tcctgctgct cctgctcctg ctgctcctgc tgctgctcct    60
gctactgctc ctgctgctcc tgttctgggt ga                                   92

<210> SEQ ID NO 12
<211> LENGTH: 94
<212> TYPE: DNA
<213> ORGANISM: Artificial Sequence
<220> FEATURE:
<223> OTHER INFORMATION: B6466

<400> SEQUENCE: 12
cgcgtcaccc agaacaggag cagcaggagc agtagcagga gcagcagcag gagcagcagg    60
agcaggagca gcaggagcag cagcacccaa aagg                                 94

<210> SEQ ID NO 13
<211> LENGTH: 86
<212> TYPE: DNA
<213> ORGANISM: Artificial Sequence
<220> FEATURE:
<223> OTHER INFORMATION: B6467

<400> SEQUENCE: 13
cgccttttgg gtgctgctgc tcctgctgct cctgctcctg ctgctcctgc tgctgctcct    60
gctactgctc ctgctgttct gggtga                                          86

<210> SEQ ID NO 14

```
<211> LENGTH: 88
<212> TYPE: DNA
<213> ORGANISM: Artificial Sequence
<220> FEATURE:
<223> OTHER INFORMATION: B6468

<400> SEQUENCE: 14
cgcgtcaccc agaacagcag gagcagtagc aggagcagca gcaggagcag caggagcagg    60
agcagcagga gcagcagcac ccaaaagg                                       88

<210> SEQ ID NO 15
<211> LENGTH: 77
<212> TYPE: DNA
<213> ORGANISM: Artificial Sequence
<220> FEATURE:
<223> OTHER INFORMATION: B6469

<400> SEQUENCE: 15
cgcctttggg gtgctgctgc tcctgctgct cctgctcctg ctgctcctgc tgctgctcct    60
gctactgttc tgggtga                                                   77

<210> SEQ ID NO 16
<211> LENGTH: 79
<212> TYPE: DNA
<213> ORGANISM: Artificial Sequence
<220> FEATURE:
<223> OTHER INFORMATION: B6470

<400> SEQUENCE: 16
cgcgtcaccc agaacagtag caggagcagc agcaggagca gcaggagcag gagcagcagg    60
agcagcagca cccaaaagg                                                 79

<210> SEQ ID NO 17
<211> LENGTH: 65
<212> TYPE: DNA
<213> ORGANISM: Artificial Sequence
<220> FEATURE:
<223> OTHER INFORMATION: B6471

<400> SEQUENCE: 17
cgcctttggg gtgctgctgc tcctgctgct cctgctcctg ctgctcctgc tgctgttctg    60
ggtga                                                                65

<210> SEQ ID NO 18
<211> LENGTH: 67
<212> TYPE: DNA
<213> ORGANISM: Artificial Sequence
<220> FEATURE:
<223> OTHER INFORMATION: B6472

<400> SEQUENCE: 18
cgcgtcaccc agaacagcag caggagcagc aggagcagga gcagcaggag cagcagcacc    60
caaaagg                                                              67

<210> SEQ ID NO 19
<211> LENGTH: 36
<212> TYPE: DNA
<213> ORGANISM: Artificial Sequence
<220> FEATURE:
<223> OTHER INFORMATION: C3208

<400> SEQUENCE: 19
tatgaattct caggatccgc gagggggcag ggcctg                              36
```

<210> SEQ ID NO 20
<211> LENGTH: 36
<212> TYPE: DNA
<213> ORGANISM: Artificial Sequence
<220> FEATURE:
<223> OTHER INFORMATION: C3209

<400> SEQUENCE: 20
gtgacgcgtg gatcaagagt gaagttcagc aggagc                              36

<210> SEQ ID NO 21
<211> LENGTH: 20
<212> TYPE: PRT
<213> ORGANISM: Artificial Sequence
<220> FEATURE:
<223> OTHER INFORMATION: TM20

<400> SEQUENCE: 21

Phe Trp Val Leu Leu Leu Leu Leu Leu Leu Leu Leu Leu Leu Leu
1               5                   10                  15

Leu Phe Trp Val
            20

<210> SEQ ID NO 22
<211> LENGTH: 24
<212> TYPE: PRT
<213> ORGANISM: Artificial Sequence
<220> FEATURE:
<223> OTHER INFORMATION: TM24

<400> SEQUENCE: 22

Phe Trp Val Leu Leu Leu Leu Leu Leu Leu Leu Leu Leu Leu Leu
1               5                   10                  15

Leu Leu Leu Leu Leu Phe Trp Val
            20

<210> SEQ ID NO 23
<211> LENGTH: 27
<212> TYPE: PRT
<213> ORGANISM: Artificial Sequence
<220> FEATURE:
<223> OTHER INFORMATION: TM27

<400> SEQUENCE: 23

Phe Trp Val Leu Leu Leu Leu Leu Leu Leu Leu Leu Leu Leu Leu
1               5                   10                  15

Leu Leu Leu Leu Leu Leu Leu Leu Phe Trp Val
            20                  25

<210> SEQ ID NO 24
<211> LENGTH: 29
<212> TYPE: PRT
<213> ORGANISM: Artificial Sequence
<220> FEATURE:
<223> OTHER INFORMATION: TM29

<400> SEQUENCE: 24

Phe Trp Val Leu Leu Leu Leu Leu Leu Leu Leu Leu Leu Leu Leu
1               5                   10                  15

Leu Leu Leu Leu Leu Leu Leu Leu Leu Leu Phe Trp Val
            20                  25

<210> SEQ ID NO 25

```
<211> LENGTH: 31
<212> TYPE: PRT
<213> ORGANISM: Artificial Sequence
<220> FEATURE:
<223> OTHER INFORMATION: TM31

<400> SEQUENCE: 25

Phe Trp Val Leu Leu Leu Leu Leu Leu Leu Leu Leu Leu Leu Leu
1               5                   10                  15

Leu Leu Leu Leu Leu Leu Leu Leu Leu Leu Leu Phe Trp Val
            20                  25                  30

<210> SEQ ID NO 26
<211> LENGTH: 25
<212> TYPE: PRT
<213> ORGANISM: Artificial Sequence
<220> FEATURE:
<223> OTHER INFORMATION: Novel Sequence

<400> SEQUENCE: 26

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25
```